United States Patent
Depuis

(10) Patent No.: US 6,616,947 B1
(45) Date of Patent: Sep. 9, 2003

(54) ENCAPSULATION SYSTEM WITH ORGANIC CORE AND MINERAL CORTEX BASED ON ALUMINIUM HYDROXYCARBONATE AND PREPARATION METHOD

(75) Inventor: Dominique Depuis, Deuil-la-Barre (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/622,209

(22) PCT Filed: Feb. 9, 1999

(86) PCT No.: PCT/FR99/00280
§ 371 (c)(1),
(2), (4) Date: Oct. 26, 2000

(87) PCT Pub. No.: WO99/40902
PCT Pub. Date: Aug. 19, 1999

(30) Foreign Application Priority Data

Feb. 13, 1998 (FR) .............................. 98 01781

(51) Int. Cl.⁷ ................................ A61K 9/50
(52) U.S. Cl. .................. 424/490; 424/455; 424/489
(58) Field of Search ................ 424/490, 455, 424/489

(56) References Cited

U.S. PATENT DOCUMENTS 3,880,901 A * 4/1975 Turner .................. 260/448
4,198,390 A * 4/1980 Rider ..................... 424/21
4,609,543 A * 9/1986 Morris et al. ............ 424/38
6,183,776 B1 * 2/2001 Depui et al. ............ 424/468

FOREIGN PATENT DOCUMENTS

| EP | 0 465 235 | 1/1992 |
| FR | 2 401 619 | 3/1979 |

* cited by examiner

Primary Examiner—Thurman K. Page
Assistant Examiner—Rachel M. Bennett
(74) Attorney, Agent, or Firm—Burns, Doane, Swecker & Mathis, L.L.P.

(57) ABSTRACT

An encapsulation system comprising: a core formed wholly or in part of at least one organic active principle; an inorganic shell formed wholly or in part of aluminum hydroxycarbonate; and wherein cohesion of the system is achieved by means of at least one nonionic surfactant comprising at least one hydrophobic segment and at least one hydrophilic segment. Also, a process for the preparation of an encapsulation system having an organic core, composed wholly or in part of at least one organic active principle, and an inorganic shell composed wholly or in part of a basic aluminum carbonate, includes: the in situ precipitation in an aqueous medium of basic aluminum carbonate, at a pH of less than 5, with stirring, in the presence of at least one nonionic surfactant, having at least one hydrophobic segment and at least one hydrophilic segment, and at least one organic active principle, the recovery of the aqueous dispersion thus formed.

41 Claims, No Drawings

ENCAPSULATION SYSTEM WITH ORGANIC CORE AND MINERAL CORTEX BASED ON ALUMINIUM HYDROXYCARBONATE AND PREPARATION METHOD

This application is a 371 of PCT/FR99/00280 filed Feb. 9, 1999.

A subject-matter of the present invention is a novel encapsulation system having an external surface which is essentially inorganic in nature, this surface being suited to the protection and/or to the controlled release of organic compound(s).

It is possible, among the encapsulation systems already available for the inclusion of organic substances, to distinguish two main types thereof:

the first system is similar to a so-called chamber system; the agent to be encapsulated is retained therein using a membrane which is conventionally polymeric in nature. These organic capsules are obtained by interfacial reaction. The size of the capsules is generally much greater than a micron;

the second system is a so-called matrix system; the agent to be encapsulated is dispersed therein in an organic network (polymer) or in a substance which is inorganic in nature (in particular silica). Mention may in particular be made, by way of illustration of this second system, of plant-protection formulations for the controlled release of insecticides with silica microcapsules (Zairyo Gijutsu, Vol. 5, No. 5 (1987) 231–236). These microcapsules of a few microns are prepared by precipitation of an alkaline silicate in the presence of a water-in-oil emulsion, the particles subsequently being calcined. The specific surfaces of the microcapsules are very high (of between 200 and 400 m$^2$/g). The active principle is introduced by adsorption on the powder with a relatively low degree of adsorption, of the order of 10%.

A specific object of the present invention is to provide a novel encapsulation system which is particularly advantageous with regard to the systems mentioned above.

The encapsulation obtained according to the present invention has, as first advantage, the advantage of protecting the encapsulated active principles from the aggressiveness of the chemical environment by bio- or ecocompatible capsules. Finally, it has in particular the advantage of making possible their release, either by diffusion or by dissolution of the shell, under the effect of a change in pH.

More specifically, the claimed encapsulation system takes advantage of the ability of basic aluminium carbonate to only dissolve from a pH of less than 5. It thus guarantees, in any host medium with a pH greater than 5, an efficient encapsulation of the organosoluble compounds which it encapsulates. In addition, basic aluminium carbonate has the advantage of having a cationic charge, which can be adjusted according to the precipitation pH. It thus proves to be possible to adjust the interactions of charges between the core constituting the encapsulation system and its shell. This is of advantage in terms of limiting the agglomeration of the particles of the encapsulated system and of quality of deposition.

The encapsulation of these active principles is carried out according to the invention by in situ precipitation of basic aluminium carbonate, constituting in all or part the inorganic shell of the capsule, in the presence of the said active principle(s) to be encapsulated.

The problem more specifically posed and solved according to the present invention related to the formation of a capsule with a shell composed of basic aluminium carbonate, and thus inorganic in nature, about an essentially organic core. It was important to find an efficient surfactant system in order, if appropriate, to stabilize the formulation per se of the active principle present at the core of the capsule and, in particular, to make possible adhesion between the core which is organic in nature and the shell based on basic aluminium carbonate, which is inorganic in nature.

The use of a nonionic surfactant composed of at least one segment with a hydrophilic nature and of at least one segment with a hydrophobic nature has made it possible to satisfactorily respond to this twofold requirement.

Consequently, a first subject-matter of the present invention is an encapsulation system comprising an organic core and an inorganic shell, characterized in that:

the core is composed, in all or part, of at least one organic active principle, the inorganic shell is composed, in all or part, of basic aluminium carbonate, and in that the cohesion of the said encapsulation system is achieved with the help of at least one nonionic surfactant comprising at least one hydrophobic segment and at least one hydrophilic segment.

Within the meaning of the present invention, the definition "surfactant comprising hydrophobic segment(s) and hydrophilic segment(s)" is understood to cover any surfactant having either units or chains which are hydrophilic or hydrophobic in nature.

Mention may in particular be made, by way of illustration but without implied limitation of these surfactants, of the following compounds:

polyalkoxylated fatty alcohols, such as polyethoxylated fatty alcohols, polyoxyalkylenated alkylphenols, such as di- or tristyrylphenols, polyvinyl alcohols or polyvinyl alkyl ethers, and block copolymers, such as polystyrene/poly(ethylene oxide).

As regards the degree of polymerization of the poly (alkylene oxide) segment present in some compounds identified above, it is generally between 2 and 50 mol and more preferably varies between 3 and 25 mol.

Preferably, this surfactant additionally has an HLB (Hydrophilic-Lipophilic Balance) value suitable for stabilizing, if appropriate, the emulsion or the dispersion of the encapsulated organic active principle(s). This HLB value is generally greater than 6 and preferably greater than 10.

More preferably, the nonionic surfactant under consideration according to the present invention is selected from polyalkoxylated alcohols, tristyrylphenols and block copolymers.

Mention will very particularly be made, by way of representation of the block copolymers which are suitable for the present invention, of the polystyrene/poly(ethylene oxide) copolymer sold under the name UPSE 1030® by the company Goldschmidt.

Among polyalkoxylated fatty alcohols, the polyethoxylated alcohol sold under the name Emulgapur LM7555® also leads to satisfactory results according to the invention.

This nonionic surfactant is generally present in the claimed encapsulation system in amounts sufficient to provide for the cohesion of the said system. It is preferably present in a proportion of approximately 1 to 3%, expressed by weight with respect to the organic components.

As regards the encapsulated active principle, it can be incorporated within the encapsulation system as is, that is to say in its native form, that is to say solid or liquid.

It is also possible to envisage incorporating it in the form of an aqueous emulsion. In this specific case, it is present in the non-continuous phase. This aqueous emulsion can be obtained in particular by incorporation of the pure active principle or of the active principle dissolved beforehand in an appropriate oil of silicone oil type, for example.

It is also possible to incorporate the active principle in the form of an aqueous dispersion.

The active principle, as is or dissolved beforehand in an oil, can generally be dispersed or emulsified at up to 70% by weight of the aqueous phase.

In both these cases, the organic active principle is preferably stabilized within the aqueous phase prior to the encapsulation.

As mentioned above, the active principle can be stabilized within the aqueous dispersion or emulsion by the nonionic surfactant according to the invention. However, it is also possible to envisage incorporating one or more other surfactants within the dispersion or emulsion.

These additional surfactants, of use in particular in dispersing, emulsifying, dissolving and/or stabilizing the various compounds to be encapsulated, can be anionic, nonionic, cationic, zwitterionic or amphoteric.

Mention may more particularly be made, by way of illustration of these compounds, of:
- anionic surfactants, such as alkyl ester sulphonates, alkyl sulphates, alkylamide sulphates and the salts of saturated or unsaturated fatty acids;
- nonionic surfactants, such as polyoxyalkylenated alkylphenols, glucosamides, glucamides or glycerolamides which are derived from N-alkylamines, polyoxyalkylenated $C_8$–$C_{22}$ aliphatic alcohols, the products resulting from the condensation of ethylene oxide with a hydrophobic compound or resulting from the condensation of propylene oxide with propylene glycol, amine oxides, alkylpolyglycosides and their polyoxyalkylenated derivatives, $C_8$–$C_{20}$ fatty amides and ethoxylated fatty acids, ethoxylated amides, ethoxylated amines or ethoxylated amidoamines;
- amphoteric and zwitterionic surfactants, such as those of betaine type, for example betaines, sulphobetaines, amidoalkyl betaines or alkyl sultaines, the condensation products of fatty acids and of protein hydrolysates, cocoamphoacetates and cocoamphodiacetates, alkyl amphopropionates or amphodipropionates, or amphoteric derivatives of alkylpolyamines.

As regards the nature of the organic compounds capable of being encapsulated in accordance with the present invention, they may be compounds of therapeutic advantage of vitamin type, compounds of use in the plant-protection field of insecticide type, or agents intended for use in cosmetics, such as fragrances, UV stabilizers, for example, and the like.

As regards more particularly the basic aluminium carbonate, it constitutes, in all or part, the shell of the claimed encapsulation system.

This is because it is possible to envisage combining it with at least one metal oxide and/or precursor of a metal oxide in the inorganic shell.

According to this alternative form, the organic core is coated with at least two distinct and consecutive inorganic layers, one based on basic aluminium carbonate and the other based on at least one metal oxide and/or precursor of a metal oxide. In this specific case, the deposition(s) of metal oxide(s) are preferably carried out following the deposition of basic aluminium carbonate.

The combination of at least one metal oxide with basic aluminium carbonate has the advantage of optimizing the diffusion of the active substances through the inorganic shell. In fact, this advantage is based on an optimization of the porosity and/or of the sensitivity of the shell to the pH.

As regards the metal oxide which can be incorporated in the inorganic shell of the encapsulation system, it can be selected from oxides or precursors of oxides of silicon, of titanium, of zirconium, of zinc, of magnesium, of yttrium, of cerium and their mixtures.

Mention may be made, as metal oxide which is particularly suitable for the present invention, of the inorganic oxides which are preferably selected from silicon, zirconium or cerium oxides and their mixtures.

They are more preferably a silica, an alumina, an aluminosilicate or one of their mixtures.

The size of the particles of the claimed encapsulation system can be of the order of a few tens of microns. It is preferably between approximately 0.1 and 10 $\mu$m.

The encapsulation system provided according to the invention generally has an inorganic charge/organic charge ratio by mass of less than or equal to 1.

Another subject-matter of the present invention is a process for the preparation of an encapsulation system having an organic core, composed in all or part of at least one organic active principle, and an inorganic shell, composed in all or part of basic aluminium carbonate, characterized in that it comprises:
- the in situ precipitation in an aqueous medium of basic aluminium carbonate, at a pH of less than 5, with stirring, in the presence of at least one nonionic surfactant, having at least one hydrophobic segment and at least one hydrophilic segment, and of at least one organic active principle,
- the recovery of the said aqueous dispersion thus formed and, if appropriate,
- its formulation in a dry form.

As regards the nonionic surfactant, it corresponds to the definition provided above in the context of the detailed description of the claimed encapsulation system.

The basic aluminium carbonate is precipitated by bringing an aqueous solution of carbonated sodium aluminate and of aluminium chloride into contact.

As regards this in situ precipitation stage, it is, of course, carried out at a pH value appropriate to resulting in precipitation of basic aluminium carbonate. Consequently, this pH must be greater than 5. It is preferably between 6 and 8. If appropriate, it may prove to be necessary to readjust the pH value during this precipitation stage.

The in situ precipitation of the basic aluminium carbonate is carried out with stirring. It is preferably carried out at room temperature. However, this temperature can vary between 25 and 70° C.

As regards the organic active principle, it is present during the in situ precipitation of the basic aluminium carbonate either in its native form or in the form of an aqueous emulsion or dispersion.

The aqueous emulsion and the aqueous dispersion of the active principle are as defined above.

The inorganic charge and the organic charge are preferably used with a ratio by mass of less than or equal to 1.

As regards the nature of the various components, in particular the nonionic surfactant, and their respective amounts used in the context of the claimed process, reference will be made to the information disclosed above during the description of the claimed encapsulation system according to the invention.

It is also possible to envisage subjecting the aqueous dispersion obtained on conclusion of the second stage of the claimed process to a fresh stage of in situ precipitation of an additional metal oxide and/or precursor of a metal oxide. It can in particular be an oxide and/or precursor as identified above. This metal oxide is preferably silica.

According to this alternative form of the claimed process, an encapsulation system comprising an inorganic shell composed of two distinct and consecutive inorganic layers is obtained, the internal layer being based on basic aluminium carbonate and the external layer being composed of at least one metal oxide and/or metal oxide precursor.

The formulation in a dry form of the aqueous dispersions obtained on conclusion of the claimed process can be carried out by any conventional method, with the proviso that the latter does not affect the stability of the encapsulated active compound or compounds.

As discussed above, the claimed encapsulation system and that capable of being obtained according to the claimed process are particularly advantageous for the protection and the controlled release of the organosoluble active principles which they comprise.

This release can be achieved either by diffusion through the pores of the encapsulation system, by dissolution of the encapsulation system under the effect of a decrease in the pH to a value of less than 5 in the external medium comprising the said system, or more conventionally by fracturing the said encapsulation system.

The second method of release is particularly advantageous in industrial fields of pharmaceutical or plant-protection type. It makes it possible to ensure the stability of the formulation for any pH value of greater than 5 and, thereby, even to adjust the diffusion of the active principle, either at a predetermined site characterized by a pH of less than 5, such as the gastric cavity for therapeutic applications, for example, or at a predetermined time by adjustment of the pH of the host medium to a value of less than 5, such as at the time of use of the corresponding plant-protection formulation.

Another subject-matter of the present invention is the use of an encapsulation system as defined or obtained according to the invention in the protection and/or the controlled release of organosoluble active principle(s).

The examples which appear below are presented by way of illustration and without implied limitation of the present invention.

EXAMPLE 1

Coating of a Polydimethylsiloxane (PDMS) Emulsion with a Shell of Basic Aluminium Carbonate Description of the emulsion (polydimethylsiloxane):

Emulsion of a silicone oil (Mirasil DM 500 000®) stabilized by an ethoxylated alcohol (Emulgapur LM 755®), sodium dodecyl sulphate SDS and Rheozan®.

SC: 44%

Viscosity: 1180 mpa·s

Size: 2.6 microns (determined using a Sympatec® pH: 5.6

Starting materials:

Solution of aluminium chloride (SPCA)

| | |
|---|---|
| Relative density | 1.52 |
| $Al_2O_3$ assay | 21.5 to 24.5% |
| $Na_2O$ assay | 17 to 19% |

Starting materials:

Solution of sodium aluminate (SPCA)

| | |
|---|---|
| Relative density | 1.5 |
| Aluminium oxide | 24% |
| Sodium oxide | 19% |

Sodium carbonate (Prolabo)

| | |
|---|---|
| Rectapur ® | 99% $Na_2CO_3$ |

Overall composition of the reaction mixture:

| | |
|---|---|
| Emulsion: | 50 g |
| Water: | 443.5 g |
| Carbonated aluminate solution | 43.5 g |
| Aluminium chloride solution | 32 g |
| The carbonated aluminate solution was prepared beforehand from: | |
| Sodium aluminate solution | 81.75 g |
| Purified water | 144.8 g |
| Sodium carbonate | 60.0 g |

Procedure 443.5 g of water and 50 g of emulsion are introduced at 25° C. into a reactor equipped with a stirrer. The pH is adjusted to 6.5 by addition of a few drops of carbonated aluminate. After stabilization of the pH at 6.5, the carbonated aluminate solution (throughput: 2 ml/mn) and the aluminium chloride solution (throughput: 1.2 ml/mn) are added simultaneously. A few minutes after the beginning of the introduction of the reactants, the suspension flocculates and the dispersion is resuspended with ultrasound. The dispersion is transferred into a reactor equipped with a stirrer and the introduction of the reactants is then continued until introduction is complete.

At the end of precipitation, the dispersion obtained is stable. The particles are washed by centrifuging and redispersed in an aqueous medium. The absence of release is characteristic of encapsulation.

The dispersion obtained exhibits a pH of 6 and a zeta potential of +20 mV. In contrast, the starting emulsion exhibits a zeta potential of −15 mV.

The inversion in charge before and after encapsulation clearly shows that a capsule based on basic aluminium carbonate has been obtained.

EXAMPLE 2

Encapsulation of Retinol 10 CM (Vitamin A) with a Shell of Basic Aluminium Carbonate Starting materials:

Retinol 10 CM ® (vitamin A: 10% in an oil)
Surfactant (emulsion): polystyrene/poly(ethylene oxide) block copolymer (UPSE 1030 ®, sold by the company Goldschmidt)
Solution of aluminium chloride (SPCA)

| | |
|---|---|
| Relative density | 1.52 |
| $Al_2O_3$ assay | 21.5 to 24.5% |
| $Na_2O$ assay | 17 to 19% |

-continued

Starting materials:

Solution of sodium aluminate (SPCA)

| Relative density | 1.5 |
|---|---|
| Aluminium oxide | 24% |
| Sodium oxide | 19% |

Sodium carbonate (Prolabo)

| Rectapur ® | 99% $Na_2CO_3$ |
|---|---|
| Sodium dodecyl sulphate (Aldrich) | 98% SDS |

| Preparation of the carbonated aluminate solution: | |
|---|---|
| Aluminate solution | 20.75 g |
| Purified water | 37 g |
| Sodium carbonate | 15 g |

The mixture is stirred for 30 minutes. It then becomes clear and ready for use.

| Preparation of the emulsion: | |
|---|---|
| Retinol 10 CM ® | 20 g (10% by mass/water) |
| USPE 1030 ® | 1.2 g |
| Purified water | 178.8 g |

The 2 opposing phases are emulsified using an Ultraturrax®. The size of the droplets is 2 microns. The pH of the emulsion is between 4 and 5.

| Overall composition of the reaction mixture: | |
|---|---|
| Emulsion | 200 g |
| Water | 200 g |
| SDS | 0.1 g |
| Carbonated aluminate solution | 72.75 g |
| Aluminium chloride solution | 50 g |

Procedure:

200 g of purified water comprising 0.1 g of SDS and 200 g of emulsion are introduced at 25° C. into a jacketed reactor equipped with a stirrer (at 300 rev/min). The pH is adjusted to 6.4 by addition of a few drops of carbonated aluminate. After stabilization of the pH at 6.4, the carbonated aluminate solution (throughput: 2.3 ml/min) and the $AlCl_3$ solution, at a variable throughput which makes it possible to regulate the pH at 6.4, are simultaneously added. The introduction of the reactants is continued until addition is complete (normal stirring).

At the end of precipitation, the dispersion obtained is stable. The particles are washed by centrifuging and redispersed in an aqueous medium. After 6 weeks, no trace of oil is observed at the surface.

The size of the final particles is in the region of 10 microns; the solids content of the dispersion is 11.73%.

EXAMPLE 3

Encapsulation of Vitamin A with Basic Aluminium Carbonate and Silica

The first stage, which consists of encapsulation of vitamin A by precipitation of basic aluminium carbonate, is described in Example 2. Encapsulation with silica is carried out on the product resulting from Example 2.

Starting materials:

Retinol encapsulated with a basic aluminium carbonate ($Al_2O_3$ 50% oil) prepared in Example 2, with the following composition:

| Expressed as $Al_2O_3$ | 3.67% |
|---|---|
| Retinol 10 CM ® | 7.33% (vitamin A 0.73%) |

Sodium silicate, Prolabo, Rectapur ®

| Relative density | 1.33 |
|---|---|
| Rm | 3.33 |
| $SiO_2$ | 26% |
| NaOH | 1 mol/l |
| $H_2SO_4$ | 30 g/l |

| Preparation of the sodium silicate solution: | |
|---|---|
| Silicate | 23 g |
| Purified water | 92 g |

| Overall composition of the reaction mixture: | |
|---|---|
| Dispersion of Example 2 | 162 g (Solids content: 11.73%) |
| Purified water | 432 g |
| Diluted silicate | 115 g |
| 1 mol/l NaOH | 52 g |
| 30 g/l $H_2SO_4$ | 60 g |

Procedure:

162 g of the dispersion of Example 2 and 432 g of purified water are introduced at 25° C into a jacketed reactor stirred at 300 rev/min. The pH is adjusted to 9 with 18 g of 1M sodium hydroxide solution. The diluted silicate, at 3 ml/min, the 1M sodium hydroxide solution and the 30 g/l sulphuric acid, with a throughput fixed at 1 ml/min (for the acid), are simultaneously added at pH 9. The introduction of the basic compounds is controlled so as to keep the pH constant during the introduction of the reactants.

After complete addition of the reactants, the mixture is left stirring at room temperature for one hour.

Subsequently, separation is carried out by centrifuging for 30 minutes at 4500 rev/min and redispersion in aqueous medium is carried out.

The supernatant does not exhibit traces of oil. No release phenomenon is therefore witnessed.

The particles can be recovered in the form of a powder after drying at 40° C.

EXAMPLE 4

Encapsulation of Fragrance with Basic Aluminium Carbonate

Starting materials:

Fragrance concentrate
Silicone oil, Rhône-Poulenc 47V20 ®
Surfactant: polystyrene/poly(ethylene oxide) block copolymer (UPSE 1030 ®, sold by the company Goldschmidt)

-continued

Starting materials:

Solution of sodium aluminate (SPCA):

| | |
|---|---|
| Relative density | 1.5 |
| Aluminium oxide | 24% |
| Sodium oxide | 19% |

Sodium carbonate (Prolabo)

| | |
|---|---|
| Rectapur ® | 99% |
| Sodium dodecyl sulphate (Aldrich) | 98% |

Preparation of the carbonated aluminate:
See Example 2

Preparation of the emulsion:

| | |
|---|---|
| Fragrance | 2 g |
| Oil 47V20 | 18 g |
| Surfactant | 1.2 g |
| Purified water | 178.8 g |

Overall composition of the mixture:

| | |
|---|---|
| Emulsion | 200 g |
| Purified water | 200 g |
| SDS | 0.1 g |
| Carbonated aluminate | 72.75 g |
| $AlCl_3$ | 50 g |

Procedure:

200 g of emulsion and 200 g of purified water comprising 0.1 g of SDS are introduced at room temperature into a jacketed reactor with stirring at 300 rev/min. The pH is adjusted to 6.4 with a few drops of carbonated aluminate. After stabilization of the pH, the carbonated aluminate is introduced at 2.3 ml/min at the same time as $AlCl_3$ at constant pH (6.4). After complete addition of the reactants, the mixture is left to mature at room temperature and with stirring for one hour.

The final suspension is stable and is separated from the aqueous mother liquors by centrifuging at 4500 rev/min for 30 minutes. The cake obtained is redispersed in purified water.

What is claimed is:

1. An encapsulation system comprising an organic core and an inorganic shell, wherein:
   the core is composed, in all or part, of at least one organic active principle,
   the inorganic shell is composed, in all or part, of basic aluminum-carbonate, and
   cohesion between the core and the inorganic shell of the encapsulation system is promoted by at least one nonionic surfactant comprising at least one hydrophobic segment and at least one hydrophilic segment, the nonionic surfactant is selected from:
   polyalkoxylated fatty alcohols,
   polyoxyalkylenated alkylphenols,
   polyvinyl alcohols or polyvinyl alkyl ethers, and
   block copolymers.

2. The system according to claim 1, wherein the nonionic surfactant is selected from polyalkoxylated alcohols, tristyrylphenols and polystyrene/poly(ethylene oxide) block copolymers.

3. The system according to claim 1, wherein the nonionic surfactant has an HLB greater than 6.

4. The system according to claim 1, wherein the nonionic surfactant is present in the encapsulation system in a proportion of approximately 1 to 3% by weight with respect to the organic components.

5. The system according to claim 1, wherein the nonionic surfactant is selected from:
   polyalkoxylated fatty alcohols,
   polyoxyalkylenated alkylphenols,
   polyvinyl alcohols or polyvinyl alkyl ethers, and
   block copolymers
   with the degree of polymerization of the poly(alkylene oxide) segment being between 2 and 50 mol.

6. The system according to claim 1, wherein the nonionic surfactant is selected from polyalkoxylated alcohols, tristyrylphenols and block copolymers.

7. The system according to claim 1, wherein the active principle is incorporated as a solid or liquid in the core of the said system.

8. The system according to claim 1, wherein the organic active principle is incorporated in the form of an aqueous emulsion or dispersion.

9. The system according to claim 1, wherein the organic active principle is incorporated in the form of an aqueous emulsion with said active principle being dissolved in a silicone oil.

10. The system according to claim 1, wherein the organic active principle is incorporated in the form of an aqueous emulsion with the active principle being dispersed or emulsified at up to 70% by weight of said aqueous phase.

11. The system according to claim 1, wherein the organic active principle is incorporated in the form of an aqueous emulsion with the active principle being stabilized within the aqueous phase with at least one additional surfactant.

12. The system according to claim 1, wherein the organic active principle is incorporated in the form of an aqueous emulsion which is stabilized with at least one additional surfactant selected from
   anionic surfacants;
   nonanionic surfactants;
   amphoteric and zwitterionic surfactants.

13. The system according to claim 1, wherein the basic aluminium carbonate is combined, in the inorganic shell, with at least one metal oxide and/or precursor of a metal oxide.

14. The system according to claim 1, wherein the basic aluminium carbonate is combined, in the inorganic shell which is composed of at least two distinct and consecutive inorganic layers, one based on basic aluminium carbonate and the other based on at least one metal oxide and/or precursor of a metal oxide.

15. The system according to claim 1, wherein the basic aluminium carbonate is combined, in the inorganic shell which is composed of at least two distinct and consecutive inorganic layers, one based on basic aluminium carbonate and the other based on at least oxides or precursors of oxides of silicon, of titanium, of zirconium, of zinc, of magnesium, of yttrium, of cerium and their mixtures.

16. The system according to claim 1, having a particle size of between approximately 0.1 and 10 μm.

17. The system according to claim 1, having an inorganic charge/organic charge ratio by mass of less than or equal to 1.

18. The system according to claim 1, wherein the nonionic surfactant is selected from:
polyethoxylated fatty alcohols,
dior tristyrylphenols, and
polystyrene/poly(ethylene oxide).

19. The system according to claim 1, wherein the nonionic surfactant is selected from:
polyethoxylated fatty alcohols,
dior tristyrylphenols, and
polystyrene/poly(ethylene oxide)
with the degree of polymerization of the poly(alkylene oxide) segment being between 2 and 50 mol.

20. The system according to claim 1, wherein the organic active principle is incorporated in the form of an aqueous emulsion which is stabilized with at least one additional surfactant selected from alkyl ester sulphonates, alkyl sulphates, alkylamide sulphates and the salts of saturated or unsaturated fatty acids;

polyoxyalkylenated alkylphenols, glucosamides, glucamides or glycerolamides which are derived from N-alkylamines, polyoxyalkylenated $C_8$–$C_{22}$ aliphatic alcohols, the products resulting from the condensation of ethylene oxide with a hydrophobic compound or resulting from the condensation of propylene oxide with propylene glycol, amine oxides, alkylpolyglycosides and their polyoxyalkylenated derivatives, $C_8$–$C_{20}$ fatty amides and ethoxylated fatty acids, ethoxylated amides, ethoxylated amines or ethoxylated amidoamines;

betaines, sulphobetaines, amidoalkyl betaines or alkyl sultaines, the condensation products of fatty acids and of protein hydrolysates, cocoamphoacetates and cocoamphodiacetates, alkyl amphopropionates or amphodipropionates, or amphoteric derivatives of alkylpolyamines.

21. A particle comprising:
a core comprising at least one active organic substance;
an inorganic shell encapsulating the core comprising basic aluminum-carbonate; and
a nonionic surfactant comprising at least one hydrophobic segment and at least one hydrophilic segment;
wherein the particle has a size of approximately 0.1 to 10 µm.

22. A process for the preparation of an encapsulation system having an organic core, composed in all or part of at least one organic active principle, and an inorganic shell, composed in all or part of basic aluminium carbonate, characterized in that it comprises:
the in situ precipitation in an aqueous medium of basic aluminium carbonate, at a pH of less than 5, with stirring, in the presence of at least one nonionic surfactant, having at least one hydrophobic segment and at least one hydrophilic segment, and of at least one organic active principle, and
the recovery of the said aqueous dispersion thus formed.

23. The process according to claim 22, wherein the basic aluminium carbonate is precipitated by bringing an aqueous solution of carbonated sodium aluminate and of aluminium chloride into contact.

24. The process according to claim 22, wherein the pH is between 6 and 8.

25. The process according to claim 22, wherein the nonionic surfactant is selected from:
polyalkoxylated fatty alcohols,
polyoxyalkylenated alkylphenols,
polyvinyl alcohols or polyvinyl alkyl ethers, and
block copolymers.

26. The process according to claim 22, wherein the nonionic surfactant is selected from:
polyalkoxylated fatty alcohols,
polyoxyalkylenated alkylphenols,
polyvinyl alcohols or polyvinyl alkyl ethers, and
block copolymers
with the degree of polymerization of the poly(alkylene oxide) segment being between 2 and 50 mol.

27. The process according to claim 22, wherein the nonionic surfactant is selected from polyalkoxylated alcohols, tristyrylphenols and block copolymers.

28. The process according to claim 22, wherein the nonionic surfactant has an HLB of greater than 6.

29. The process according to claim 22, wherein the nonionic surfactant is present in the encapsulation system in a proportion of approximately 1 to 3 %, expressed by weight with respect to the organic components.

30. The process according to claim 22, wherein the active principle is present, during the in situ precipitation of the basic aluminium carbonate, as a solid or liquid or in the form of an aqueous emulsion or dispersion.

31. The process according to claim 22, wherein the active principle is present, during the in situ precipitation of the basic aluminium carbonate in the form of an aqueous emulsion which comprises the said active principle dissolved in a silicone oil.

32. The process according to claim 22, wherein the active principle is present, during the in situ precipitation of the basic aluminium carbonate, as a solid or liquid or in the form of an aqueous emulsion or dispersion with the active principle being dispersed or emulsified at up to 70% by weight of the aqueous phase.

33. The process according to claim 22, wherein the active principle is present, during the in situ precipitation of the basic aluminium carbonate, as a solid or liquid or in the form of an aqueous emulsion or dispersion with the active principle being stabilized within the aqueous phase with at least one additional surfactant.

34. The process according to claim 22, wherein the active principle is present, during the in situ precipitation of the basic aluminium carbonate, as a solid or liquid or in the form of an aqueous emulsion or dispersion with the active principle being stabilized within the aqueous phase with at least one additional surfactant selected from:
anionic surfactants;
nonionic surfactants;
amphoteric and zwitterionic surfactants.

35. The process according to claim 22, wherein the inorganic charge and the organic charge are used with a ratio by mass of less than or equal to 1.

36. The process according to claim 22, wherein the dispersion obtained on conclusion of the second stage is subjected to a fresh stage of in situ precipitation of a metal oxide and/or precursor of a metal oxide.

37. The process according to claim 22, wherein the dispersion obtained on conclusion of the second stage is subjected to a fresh stage of in situ precipitation of a metal oxide and/or precursor of a metal oxide with the precipitated metal oxide being silica.

38. The process according to claim 22, further comprising: drying the recovered aqueous dispersion.

39. The process according to claim 22, wherein the nonionic surfactant is selected from:
   polyethoxylated fatty alcohols,
   di- or tristyrylphenols, and
   polystyrene/poly(ethylene oxide).

40. The process according to claim 22, wherein the nonionic surfactant is selected from:
   polyethoxylated fatty alcohols,
   dior tristyrylphenols, and
   polystyrene/poly(ethylene oxide)
with the degree of polymerization of the poly(alkylene oxide) segment being between 2 and 50 mol.

41. The process according to claim 22, wherein the active principle is present, during the in situ precipitation of the basic aluminium carbonate, as a solid or liquid or in the form of an aqueous emulsion or dispersion with the active principle being stabilized within the aqueous phase with at least one additional surfactant selected from:

alkyl ester sulphonates, alkyl sulphates, alkylamide sulphates and the salts of saturated or unsaturated fatty acids;

polyoxyalkylenated alkylphenols, glucosamides, glucamides or glycerolamides which are derived from N-alkylamines, polyoxyalkylenated $C_8$–$C_{22}$ aliphatic alcohols, the products resulting from the condensation of ethylene oxide with a hydrophobic compound or resulting from the condensation of propylene oxide with propylene glycol, amine oxides, alkylpolyglycosides and their polyoxyalkylenated derivatives, $C_8$–$C_{20}$ fatty amides and ethoxylated fatty acids, ethoxylated amides, ethoxylated amines or ethoxylated amidoamines;

betaines, sulphobetaines, amidoalkyl betaines or alkyl sultaines, the condensation products of fatty acids and of protein hydrolysates, cocoamphoacetates and cocoamphodiacetates, alkyl amphopropionates or amphodipropionates, or amphoteric derivatives of alkylpolyamines.

* * * * *